(12) United States Patent
Harding et al.

(10) Patent No.: US 8,282,046 B2
(45) Date of Patent: Oct. 9, 2012

(54) SYSTEMS AND METHODS FOR ORGANIZING AND PRIMING AN IV ADMINISTRATION SET

(75) Inventors: Weston F. Harding, Lehi, UT (US); Bryan G. Davis, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 396 days.

(21) Appl. No.: 12/370,344

(22) Filed: Feb. 12, 2009

(65) Prior Publication Data

US 2010/0200706 A1  Aug. 12, 2010

(51) Int. Cl.
*F16L 3/00* (2006.01)

(52) U.S. Cl. ............ 248/49; 248/75; 248/301; 248/304

(58) Field of Classification Search .............. 248/49, 248/75, 301, 304; 604/80, 82, 174
See application file for complete search history.

(56) References Cited

U.S. PATENT DOCUMENTS

| | | | | |
|---|---|---|---|---|
| 2,954,028 | A | * | 9/1960 | Smith .............................. 604/80 |
| 4,406,042 | A | | 9/1983 | McPhee |
| 4,589,171 | A | | 5/1986 | McGill |
| 4,610,781 | A | * | 9/1986 | Bilstad et al. ................... 210/85 |
| 4,625,494 | A | * | 12/1986 | Iwatschenko et al. .......... 53/432 |
| 4,795,429 | A | | 1/1989 | Feldstein |
| 4,997,149 | A | * | 3/1991 | Koch .............................. 248/100 |
| 5,131,537 | A | | 7/1992 | Gonzalez |
| 5,188,588 | A | * | 2/1993 | Schoendorfer et al. ....... 604/6.07 |
| 5,309,604 | A | | 5/1994 | Poulsen |
| 5,389,082 | A | | 2/1995 | Baugues et al. |
| 5,419,770 | A | | 5/1995 | Crass et al. |
| 5,423,769 | A | * | 6/1995 | Jonkman et al. .............. 604/250 |
| 5,435,448 | A | | 7/1995 | Kempen |
| 5,542,160 | A | | 8/1996 | Arndt |
| 5,906,598 | A | * | 5/1999 | Giesler et al. ................. 604/251 |
| 6,015,119 | A | | 1/2000 | Starchevich |
| 6,283,945 | B1 | | 9/2001 | Bierman |
| D479,328 | S | | 9/2003 | Reynolds et al. |
| 7,160,087 | B2 | | 1/2007 | Fathallah et al. |
| 2008/0097333 | A1 | | 4/2008 | Henning |

FOREIGN PATENT DOCUMENTS

| | | |
|---|---|---|
| DE | 196 22 050 A1 | 12/1997 |
| WO | 2005/104776 A2 | 11/2005 |
| WO | 2006/083359 A2 | 8/2006 |
| WO | 2008/027157 A1 | 3/2008 |

* cited by examiner

*Primary Examiner* — Amy J Sterling
(74) *Attorney, Agent, or Firm* — Mony R. Ghose; Craig Metcalf; Kirton McConkie

(57) ABSTRACT

A device having a surface on which an intravenous administration set is organized and temporarily retained in a desired configuration to prevent undesirable tangling during setup of the set. The device further includes a plurality of clips to retain various components of the intravenous administration set in a desired orientation to improve priming of the components. The intravenous administration set is released from the device by pulling a terminal end of the set in a direction away from the device.

10 Claims, 11 Drawing Sheets

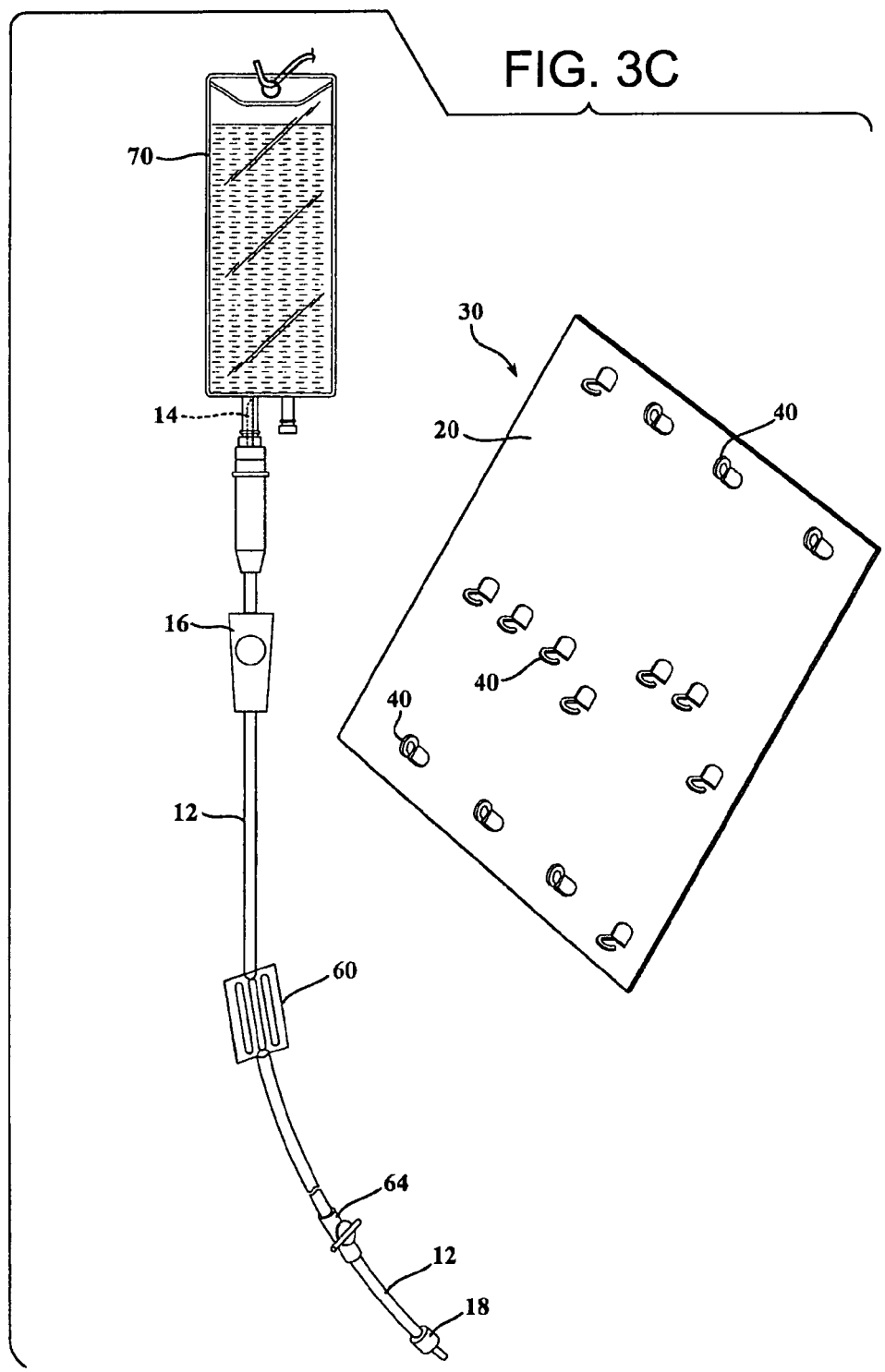

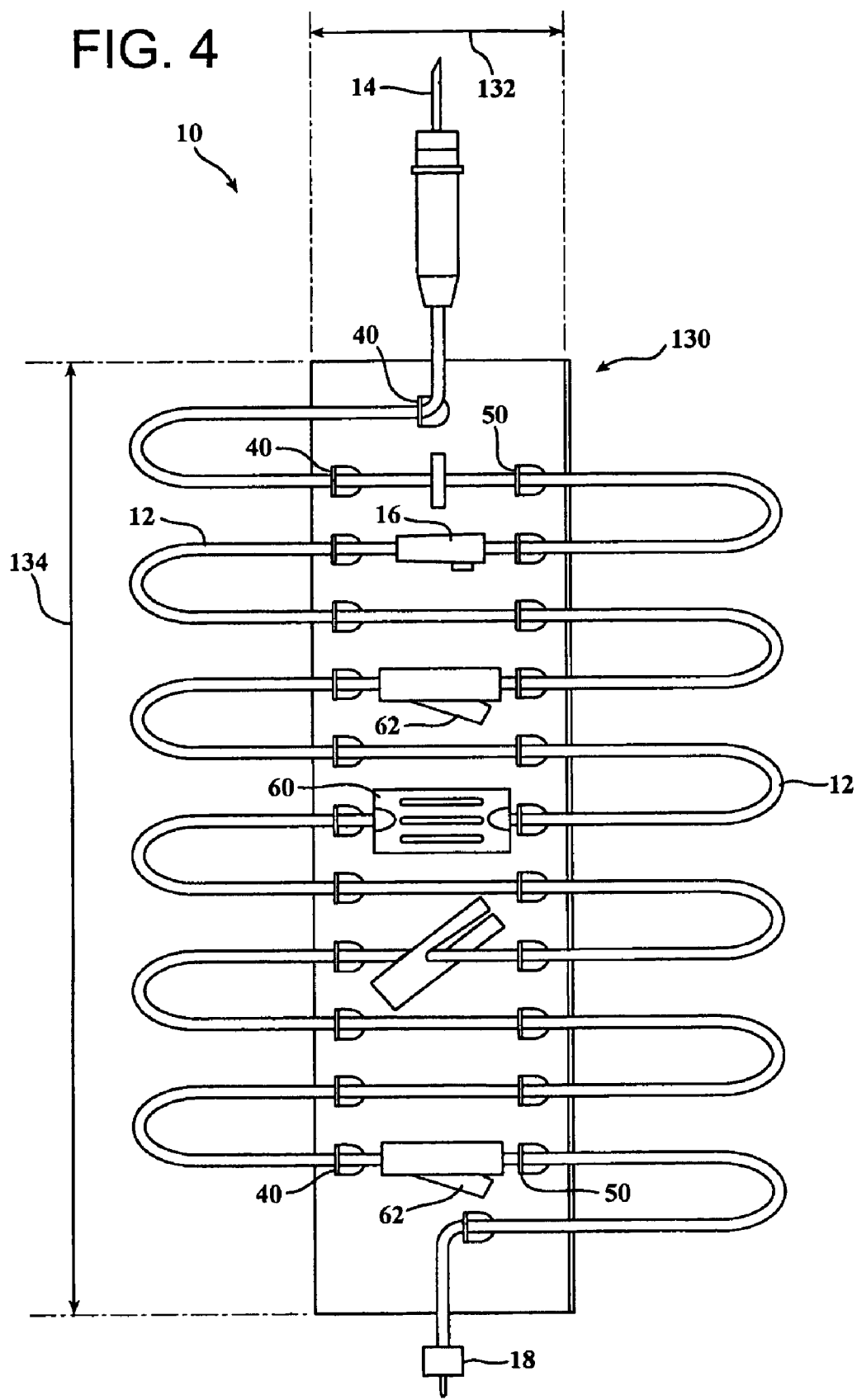

SYSTEMS AND METHODS FOR ORGANIZING AND PRIMING AN IV ADMINISTRATION SET

BACKGROUND OF THE INVENTION

The present invention relates to systems and methods for organizing and priming an intravenous (IV) administration set, as commonly used in the medical and infusion therapy fields. An IV administration set is used to deliver to or retrieve from a patient a fluid, such as blood, a medicament, a nutritional supplement, or a solution.

The IV set generally includes a section of intravenous tubing having a first end for accessing a fluid reservoir, and a second or terminal end adapted for insertion into the patient. The IV set may further include various components positioned along the section of intravenous tubing. These components are designed to control the flow of or treat the fluid within the IV set during the infusion process. For example, the IV components may include clamps, filters, chambers, access ports, stopcocks, valves, pumps, monitors, or centrifuges. Additionally, the IV set may include multiple sections or lines of intravenous tubing. Each of these components provide a desired function to the IV set and require precise organization and priming for optimal use.

An IV administration set usually ranges from 40 to 110 inches in length and comes rolled up in a packaging material. The process for preparing an IV set for use requires a clinician or user to first open the package and locate the ends of the set. Current packaging techniques typically require the user to unroll and untangle the IV set during this process. In addition to the overall length of the IV set, the various geometries and shapes of the IV components provide a plurality of surfaces that commonly entangle and catch on one another. The process of untangling the IV set will commonly result in portions of the IV set touching the ground or other unsanitary surfaces.

Once the IV set is organized and the ends located, the user must prime the intravenous tubing and components of the IV set. The process of priming ensures that any air within the IV system is purged and replaced with a priming solution prior to connecting the IV set to a patient. Thorough priming of the IV set is required for optimal performance of the IV set. The process of priming the IV set first requires the user to attach the terminal end of the set to any extension set, stopcock, or other addition component desired. The user then engages a clamp to occlude flow of fluid in the set, for example a roller clamp, a slide clamp, or a pinch clamp. The user then inserts the first end or the spike into an IV bag or fluid reservoir. At this point the user primes a drip chamber of the IV set and releases the clamp to initiate flow through the IV set.

As the fluid flows through the IV set certain areas of the IV set commonly entrap air bubbles. Entrapped air within the IV set is undesirable for many reasons. For example, some IV components rely on the absence of air to perform properly. Additionally, the presence of air may occlude or otherwise prevent proper flow of the fluid through the IV set. Entrapped air may also unexpectedly dislodge during the infusion process and enter the circulatory system of the patient, causing undesirable complications, including a stroke or death.

Entrapped air may be dislodged during the priming process by tapping portions of the IV set while allowing the fluid to continue to flow though the IV set and into a trash can or sink. The tapping forces the bubbles into the flow of fluid and out of the terminal end. In addition to wasting the fluid, the terminal end commonly contacts the unsanitary surfaces of the trash can or the sink leading to contamination of the IV set.

Thus, while techniques currently exist that are used for organizing and priming an IV administration set, challenges still exist. Accordingly, it would be an improvement in the art to augment or even replace current techniques with other techniques.

BRIEF SUMMARY OF THE INVENTION

The present invention relates to systems and methods for organizing and priming an intravenous (IV) administration set, as commonly used in the medical and infusion therapy fields. An IV administration set is used to deliver to or retrieve from a patient a fluid, such as blood, a medicament, a nutritional supplement, or a solution.

Specifically, the present invention includes various structures and methods for packaging or organizing an IV set in a desired configuration. In some implementations of the present invention, a device is provided that permits an IV set to be clipped or otherwise attached to the device in a desired configuration. The desired configuration provides at least two benefits over the prior art.

For example, a desired configuration organizes the various components and tubing to prevent entanglement of the IV set. When organized, various portions of the IV set are easily located and readily accessible further aiding the clinician in preparing the IV set for use. Additionally, a desired configuration provides optimal orientation of the various IV components of the IV set. Due to various variations in the geometry and structure of the various IV components, each component may include a preferred spatial orientation to aid priming the components. For example, in some embodiments of the present invention a first IV component of an IV set is optimally primed when the component is oriented in a horizontal axis, and a second IV component of the IV set is optimally primed in a vertical axis.

Some implementations of the present invention include a device having a planar surface for receiving and retaining the IV set in a desired configuration. The configuration of the IV set is determined and executed based upon the orientation needs of the individual components of the IV set. In some embodiments, the IV set is retained on the device via a plurality of clips. In other embodiments, the IV set is retained on the device throughout the priming process to aid in maintaining the desired orientation of the various components of the IV set. Yet in other embodiments, the terminal end of the IV set is pulled in a downward direction to release the IV set from the clips, thereby removing the IV set from the planar surface of the device. In other embodiments the planar surface includes a plurality of separate sections, each section being designed to hold a portion of the IV set. Still, in other embodiments a surface portion of an IV component is modified to include a clip, whereby a portion of the IV set is held in a desired configuration via the clip of the IV component. Finally, in other embodiments a package, such as a plastic or paper bag, is modified to include a plurality of clips for maintaining the placement of the ends of the IV set in desired locations.

In some implementations of the present invention, utilization of the organizing device provides an improved method for preparing an IV set for use with a patient. Some embodiments include the steps of opening highlighted or marked portions of the packaging material to locate a clamp of the IV set; engaging the clamp to occlude flow through the IV set; opening a highlighted or marked portion of the packaging material to locate the spike component of the IV set; attaching the spike component to a fluid reservoir and allowing the device retaining the IV set to hang from the fluid reservoir;

opening a highlighted or marked portion of the packaging material to locate the terminal end of the IV set; attaching the terminal end to any extension set, stopcock, or other addition to the IV set; priming the drip chamber; opening the clamp to initiate flow through the IV set to prime the IV set; pulling the terminal end from the device wherein the IV set unzips from the device as the clips release; removing the terminal end dust cap and connecting the terminal end to the patient. In some embodiments, the terminal end dust cap further includes an auto-prime filter that is permeable to air but prevents the passage of liquid. As such, the auto-prime filter permits the IV system to optimally prime by exhausting air within the IV set, yet prevents liquid from exiting the terminal end.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 3C is a perspective view of an implementation of an IV set organizer following removal of the IV set from the IV set organizer.

FIG. 4 is a perspective view of an implementation of a strip organizer retaining an IV administration set in a desired configuration.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
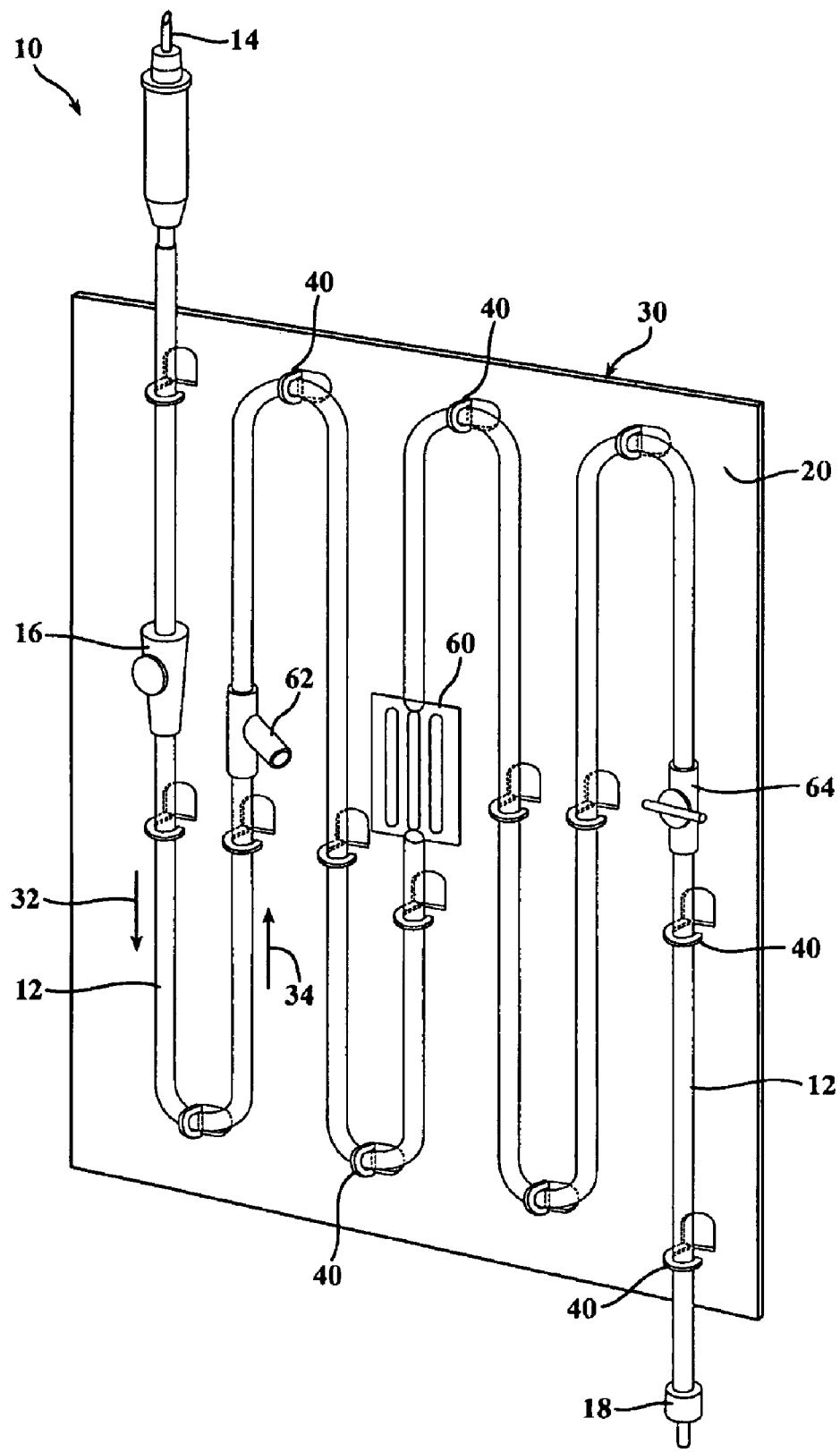
FIG. 1 is a perspective view of an implementation of an IV set organizer retaining an IV set in a desired configuration.

Referring now to FIG. 1, an implementation of an IV administration set 10 is shown in an organized configuration on an organizing surface 20 of an IV set organizer 30. Some embodiments of the IV administration set 10 generally include a section of intravenous tubing 12 having various components and features to aid a technician in administering a solution or medicament to a patient. For example, in some embodiments the IV administration set 10 includes a spike 14 for establishing fluid communication with a fluid reservoir, such as an IV bottle or bag. In other embodiments, the IV administration set 10 includes a roller clamp 16 to control or limit the flow of a fluid through the IV set 10. Embodiments of the IV set 10 may also include a male luer 18 for attaching an extension set, a stopcock, or other addition (not shown) to the IV set 10. Finally, additional components of the IV set 10 may include hemodialysis components, filters, needle free injection sites, precision filters, injection sites, luer locks, and various chambers, such as burette chambers, blood chambers, and non-vented chambers. The choice and combination of IV components will vary greatly dependent upon the intended use of the IV administration set 10.

As discussed above, an important procedural step in effectively preparing and using an IV administration set 10 is to prime the intravenous tubing 12 and the various IV components. The process of priming the IV set 10 ensures that air is purged from the set 10 prior to using the set 10 to administer a medicament to the patient. In addition to being dangerous to the patient, air within the IV set 10 can disrupt the flow of the medicament or liquid through the set 10. Thus, it is desirable and important to thoroughly prime the IV set 10 as a first step to preparing the set 10 for use with a patient.

Prior to priming the IV set 10, the IV tubing 12 and the various IV components are filled with air. The air is pushed out from the set 10 as a liquid is introduced at one end 10 and allowed to run through the set 10 to the opposite end 18. The fluid pathway through the internal structures of the IV components will commonly prevent complete purging of the air within the components. Efficient priming is often dependent upon the unique fluid pathway through the IV component. Depending upon the orientation of the component, the orientation of the fluid pathway may encourage or discourage efficient purging of the air within the pathway.

A technician will commonly be required to manually rotate the individual components to various desired orientations, or strike the components to physically dislodge the air, thereby aiding the fluid to prime the components. This process is time consuming and inefficient. With continued reference to FIG. 1, some embodiments of the present invention provide an IV administration set 10 maintained in a desired configuration via an IV set organizer 30.

The IV set organizer 30 generally includes a plurality of clips 40 and an organizing surface 20 to support an IV set 10 in a desired configuration. The organizing surface may include any material and configuration capable of maintaining a desired orientation of the IV set 10 and the various components. Examples of various implementations of the organizing surface and clips are shown and discussed in connection with FIGS. 2 and 4-9, below. In some embodiments the organizing surface 20 comprises a generally planar paperboard or cardboard material. In other embodiments, the organizing surface 20 comprises a polymer material, such as polypropylene, polyethylene, or polystyrene. The overall dimensions of the organizing surface 20 is determined by one of ordinary skill in the art, and is selected to provide a sufficient surface on which to retain the IV set 10 in a desired configuration. In some embodiments, the organizing surface 20 comprises an outer surface portion of an IV component, as shown in FIG. 8.

Figure 2A:
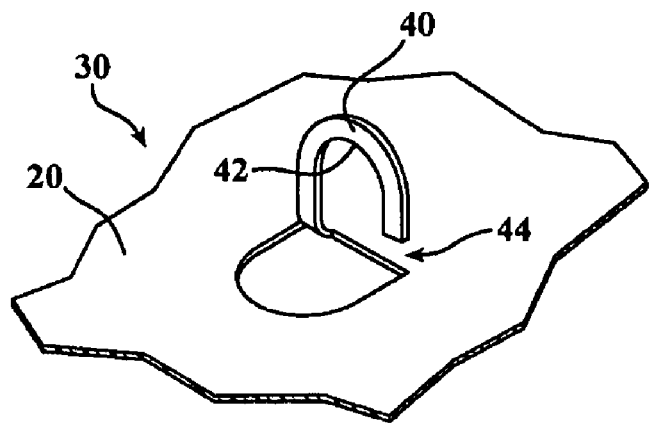
FIG. 2A is a perspective view of an implementation of a clip of the present invention.

Referring now to FIG. 2A, a detailed view of an implementation of a clip 40 is shown. In some embodiments of the present invention, the clip 40 comprises a cut-out or formed portion of the organizing surface 20. As such, a portion of the clip 40 is attached to the organizing surface 20 to effectively anchor a portion of the IV set 10 to the organizing surface 20. Formation of the clip 40 may be achieved by stamping the organizing surface 20, joining material to the organizing surface via an adhesive or plastic welding, or may include shaping the organizing surface by various plastic molding techniques, as known in the art.

Figure 2B:
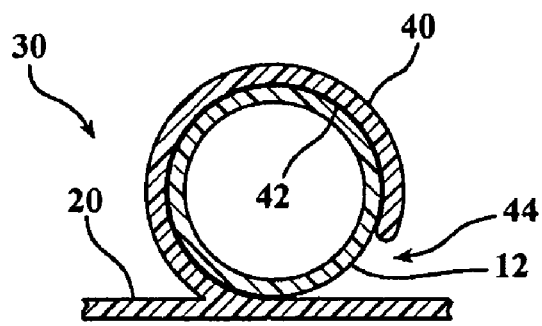
FIG. 2B is a cross-sectional side view of an implementation of a clip of the present invention.

In some embodiments the clip 40 includes a hooked surface 42 configured to compatibly receive a portion of the intravenous tubing 12, as shown in FIG. 2B. The clip 40 further includes an opening 44 whereby the intravenous tubing 12 enters and exits the clip 40. Thus, the clip 40 may be used to temporarily retain portions of the IV set 10 in a desired configuration. In other embodiments (not shown), the clip 40 is configured to retain a component of the IV set 10, such as to retain a portion of the roller clamp, the filter, the chamber, or another component.

Figure 2C:
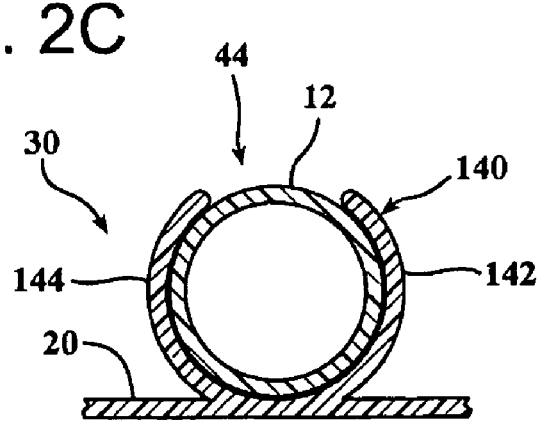
FIG. 2C is a cross-sectional side view of an implementation of a clip of the present invention.

Referring now to FIG. 2C, another embodiment of a clip 140 is shown. In this embodiment, clip 140 includes two opposing arms 142 and 144 to provide a partially opened surface for retaining a portion of the intravenous tubing 12. One having ordinary skill in the art will appreciate that various other means and techniques may be used to retain the IV set 10 to the organizing surface 20 in a desired configuration. For example, in some embodiments a temporary adhesive is used to temporarily attach the IV set 10 to the organizing surface 20. In other embodiments, the IV set 10 is permanently attached to the organizing surface 20 in the desired configuration.

Figure 3A:
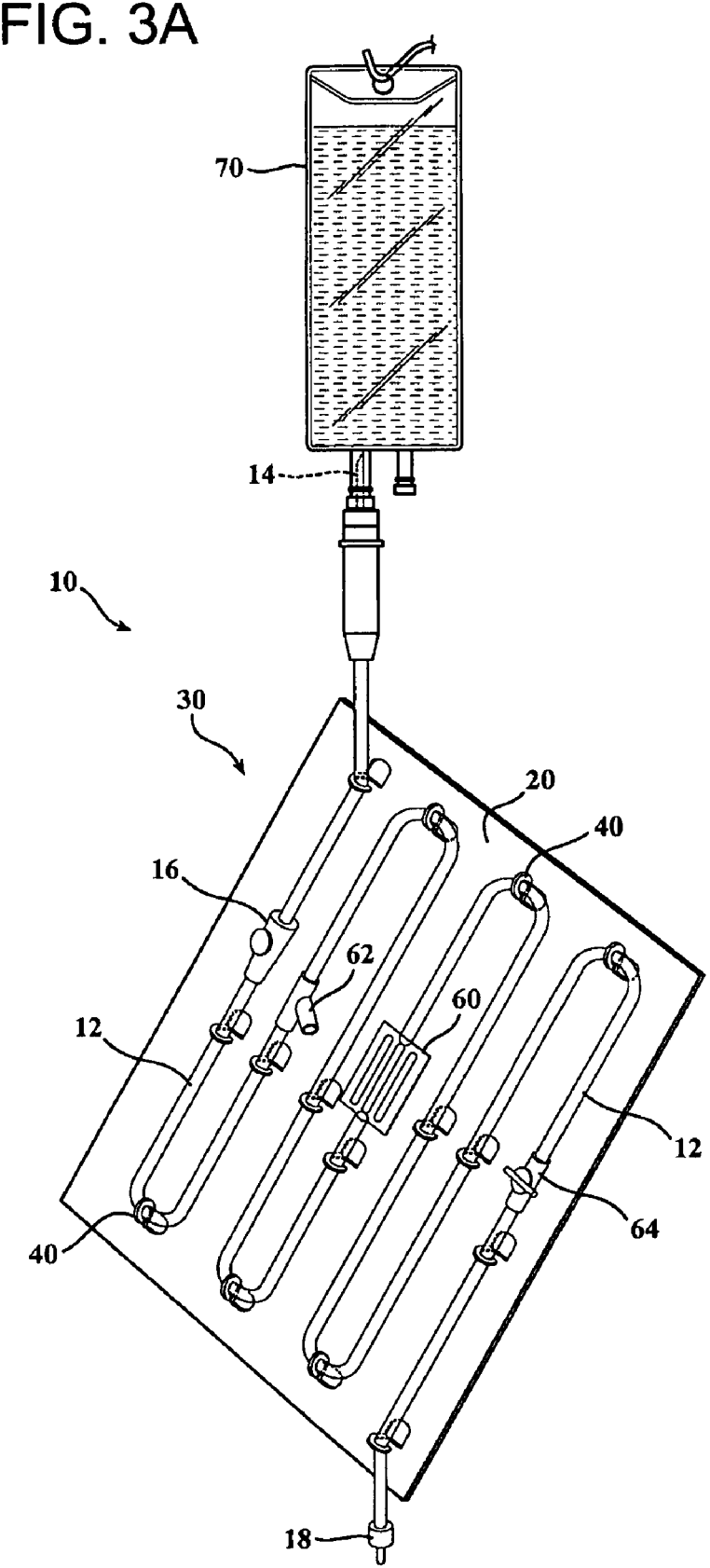
FIG. 3A is a perspective view of an implementation of an IV set organizer attached to a fluid reservoir during a priming process.

Referring now to FIGS. 1 and 3A, an IV administration set 10 is shown in an organized configuration on an organizing surface 20 of an IV set organizer 30. In addition to retaining the IV set 10 in a desired configuration, the organizing surface 20 permits accurate placement of the terminal ends 14 and 18 of the set 10. Controlled placement of the terminal ends 14 and 18 provides easy and clear access to the terminal ends 14 and 18 thereby eliminating confusion and tangles commonly encountered during the priming process. Additionally, by selectively placing the terminal ends 14 and 18 in desired locations, a technician is able to prime the IV set 10 while the IV set 10 is secured to the organizing surface 20. This feature is desirable for several reasons. For example, while the IV set 10 is secured to the organizing surface 20, the intravenous tubing 12 and the various components remain untangled and organized. Additionally, the tubing 12 and the various components are in physical and visual proximity to one another thereby assisting the technician in observing and monitoring the priming process. Finally, while the IV set 10 is secured to the organizing surface 20, the clips maintain a desired orientation of the tubing 12 and the various components thereby ensuring complete priming of the set 10.

In addition to proper orientation of the IV set 10, the ability to completely purge air from the tubing 12 and IV components is dependent upon the priming speed. The priming speed is the speed at which a priming fluid moves through the IV set 10 during the priming process. As priming fluid moves in a downward direction through the IV set 10, gravity naturally accelerates the fluid. The priming speed slows down as the priming fluid moves upward, again due to the effects of gravity. Increased priming speed increases the contact angle of the priming fluid with respect to the inner surface of the tubing 12, thereby decreasing the surface tension of the priming solution. This increased contact angel provides a pronounced convex meniscus for the leading edge of the priming fluid which fails to displace air within the IV set.

In some embodiments, the priming process is improved by slowing down and normalizing the priming speed by controlling the distance which the priming fluid travels in a downward direction. For example, in FIGS. 1 and 3A the configuration of the IV set 10 provides a series of complimenting downward 32 and upward 34 flows to normalize the overall speed of the priming fluid throughout the IV set 10. Additionally, the configuration of the IV set 10 serves to provide desired orientations for the various IV components 16, 60, 62 and 64. For example, in some implementations of the present invention the y-port 62 is adequately primed in an upward flow direction 34. In other implementations the three-way valve 64 is adequately primed in a downward flow direction 32. Yet in another implementation of the present invention, the filter 60 is optimally primed in an upward flow direction 34. One of skill in the art will appreciate that various IV components may require different orientations to achieve a desired priming of the IV set 10.

Referring now to FIG. 3A, an IV administration set 10 is shown in an organized configuration, on an organizing surface 20 of an IV set organizer 30, and coupled to a fluid reservoir 70. In some embodiments of the present invention the spike 14 of the IV set 10 is inserted into the fluid reservoir 70 and the IV set is primed while hanging from the fluid reservoir 70. As such, the intravenous tubing 12 and the various IV components are maintained in a kempt, orderly, and properly oriented configuration. Additionally, the confinement of the IV set 10 to the IV set organizer 30 provides quick location and access to the terminal ends 14 and 18. This is especially useful where the IV set 10 is particularly lengthy or includes many IV components that may become easily tangled or snagged. In some embodiments, the specific configuration of the IV 10 set on the organizing surface 20 is selected and planned based on the final spatial orientation of the IV set 10 during the priming process.

Figure 3B:
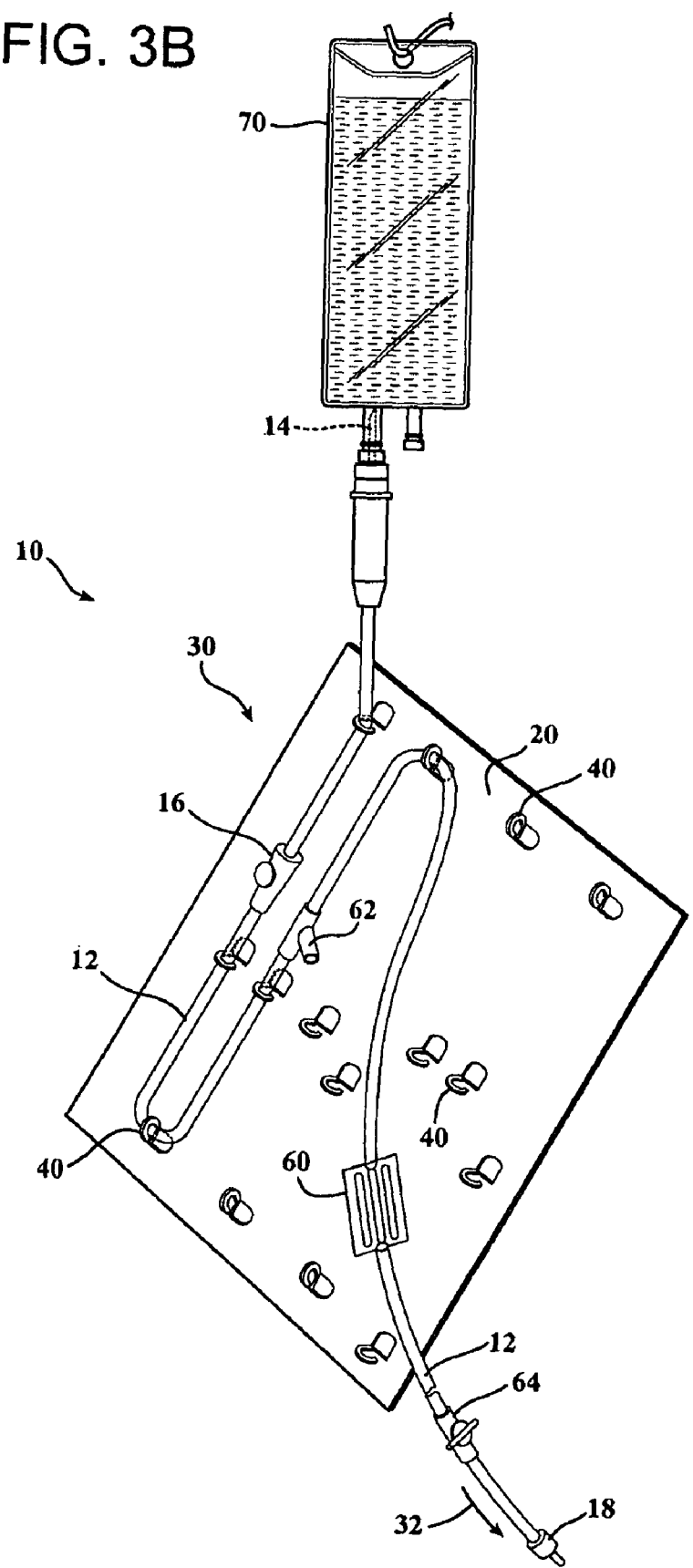
FIG. 3B is a perspective view of an implementation of an IV set organizer during removal of the IV set from the IV set organizer.

Referring now to FIG. 3B, the primed IV set 10 is removed from the IV set organizer 30 by pulling the unattached, terminal end 18 in a downward direction 32. As the terminal end 18 is pulled in a downward direction 32, the portions of the intravenous tubing 12 that are held by the clips 40 are released through the openings 44 of the clips 40. In some embodiments of the present invention, the IV set 10 is completely removed from the IV set organizer 30, as shown in FIG. 3C. The emptied IV set organizer 30 may be reused, recycled, or disposed, as desired.

Referring now to FIG. 4, an implementation of the present invention is shown incorporating an IV set strip organizer 130. The IV set strip organizer 130 comprises a singular strip having a width 132 and a height 134 sufficient to secure the various IV components of the IV set 10 in a desired configuration. It may be noted that the width 132 of the strip organizer 130 is narrower than the overall width of the intravenous tubing 12. As such, the intravenous tubing 12 is permitted to dangle beyond the edges of the organizer 130. The IV set is retained on the strip organizer 130 via a plurality of clips 40 and 50.

In some embodiments, a first clip 40 is place on a first side of each IV component, and an opposing clip 50 is placed on a second side of each IV component. As such, the IV component is retained on the organizing surface 20 of the strip organizer 30 in a desired order and configuration. The specific orientation of each IV component is selected and set based upon the optimal flow orientation required by the individual IV component. Following the priming process, the terminal end 18 is pulled in a downward direction 32 to release the IV set from the strip organizer 30. The emptied strip organizer 130 may be reused, recycled, or disposed, as desired.

Figure 5:
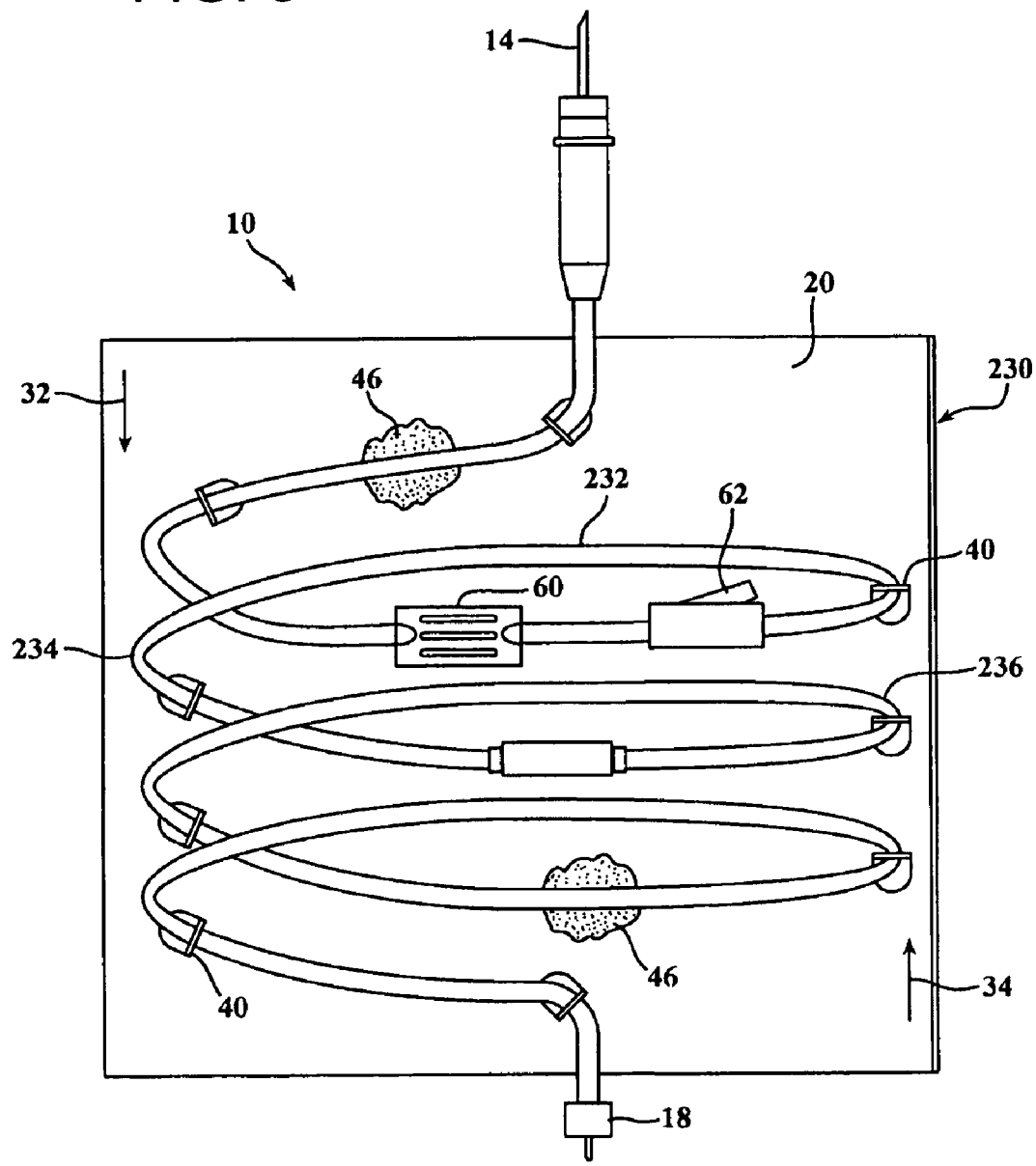
FIG. 5 is a perspective view of an implementation of spiral organizer retaining an IV administration set in a spiral configuration.

Referring now to FIG. 5, an implementation of the present invention is shown incorporating a spiral organizer 230. The spiral organizer 230 provides an organizing surface 20 on which the IV set 10 is positioned in a spiral configuration. The spiral organizer 230 is particularly useful for exceedingly long IV sets 10, or for IV sets 10 that include various IV components requiring various flow orientations and speeds. For example, the spiral configuration provides multiple flow regions 232, 234, and 236 of intravenous tubing 12 having various fluid flow properties. Horizontal regions 232 of the intravenous tubing 12 provide a moderate flow rate in a horizontal flow direction. Downward regions 234 of the intravenous tubing 12 provide an increased flow rate in a downward flow direction 32, while upward regions 236 provide decreased flow rate in an upward flow direction 34.

The spiral configuration further provides 360° of available tubing 12 on which to situate any number of IV components in a desired orientation. The overlapping sections of tubing 12 are positioned such that the IV set 10 is easily removed from the spiral organizer 230 by pulling the terminal end 18 in a downward direction 32. The sequence in which the tubing 12 is overlapped prevents the IV set 10 from tangling upon removal of the IV set 10 from the spiral organizer 230. In some embodiments, clips 40 are randomly positioned to retain the IV set 10 in the spiraled configuration. In other embodiments, a combination of clips 40 and temporary adhesive 46 are used to secure the IV set 10. Finally, in some embodiments the IV set 10 is secured in the spiraled configuration with temporary adhesives 46.

Figure 6:
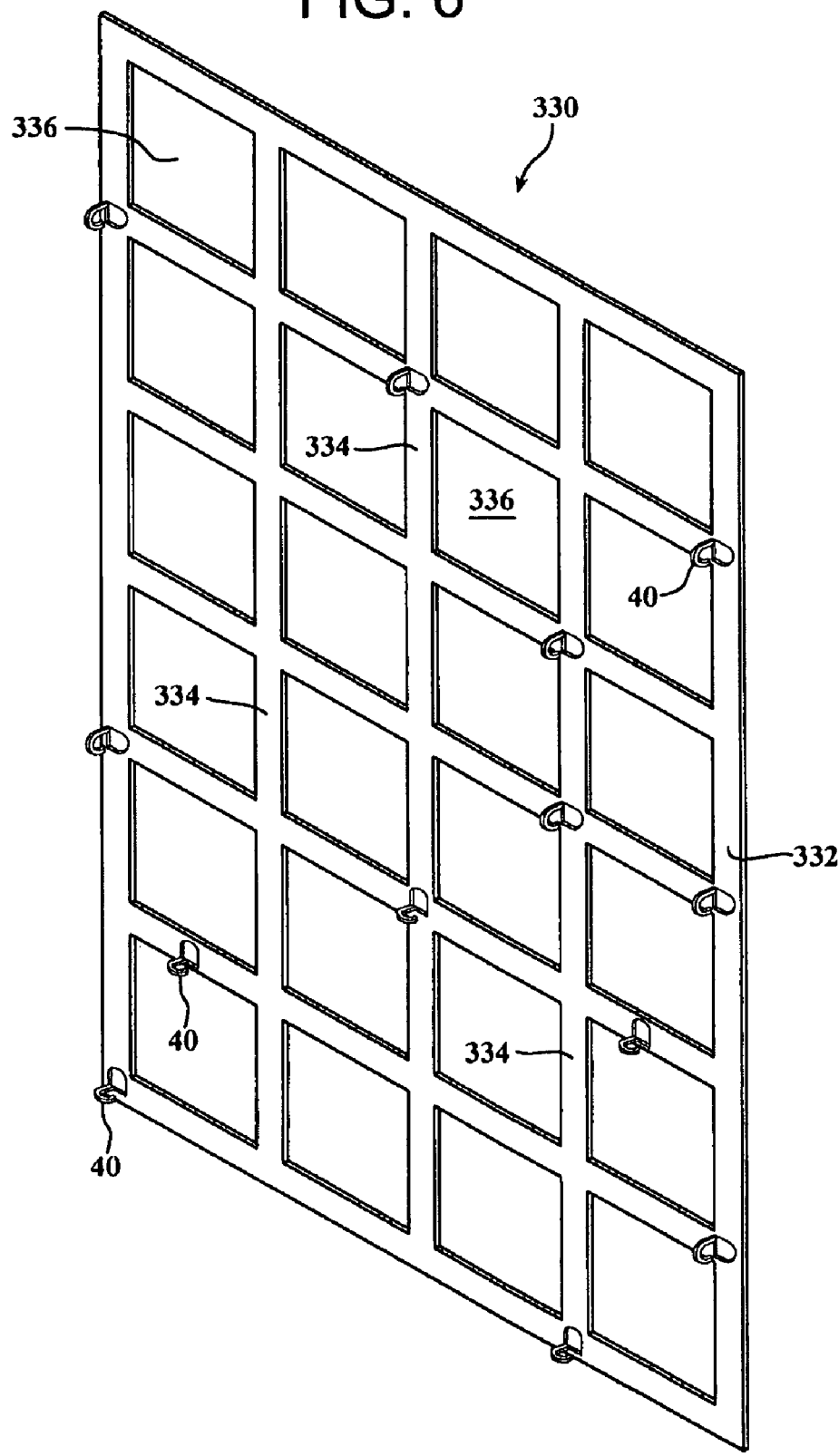
FIG. 6 is a perspective view of an implementation of a framed organizer.

Referring now to FIG. 6, a framed organizer 330 is shown. The framed organizer 330 may comprise any material structurally capable of securing and maintaining an IV administration set 10 in a desired configuration. For example, in some embodiments the framed organizer 330 is comprised of a polymer material. In other embodiments, the framed organizer 330 is comprises of a cardboard or paperboard material. Finally, in some embodiments the framed organizer 330 is comprised of a metallic material, such as aluminum or an aluminum alloy. The framed organizer 330 may also comprise a rigid or semi-rigid material.

The framed organizer 330 generally comprises a lattice structure having an outer frame 332 and an inner matrix 334 characterized by a plurality of windows 336 or spaces. In some embodiments of the present invention, framed organizer 330 includes a plurality of clips 40 randomly positioned on the frame 332 and the inner matrix 334 portions of the organizer. In some embodiments only a portion of the clips 40 are used to secure an IV set 10 to the framed organizer 330 in a desired configuration. In other embodiments, all of the clips 40 are used to secure an IV set 10 to the framed organizer 330 in a desired configuration. Finally, some embodiments a first group of clips 40 is used to secure a first IV set to the framed organizer 330, and a second group of clips 40 is used to secure a second IV set the framed organizer 330.

Figure 7:
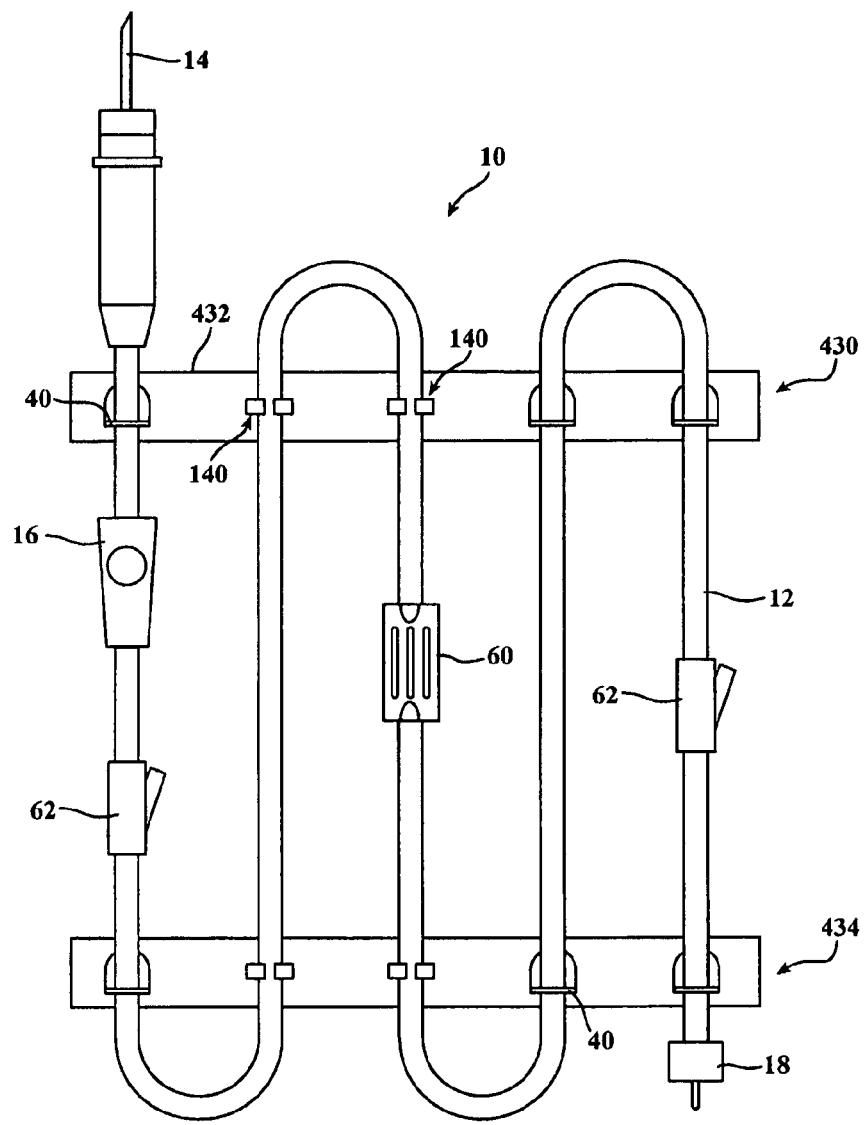
FIG. 7 is a perspective view of an implementation of a multi-sectional organizer retaining an IV administration set in a desired configuration.
Figure 8:
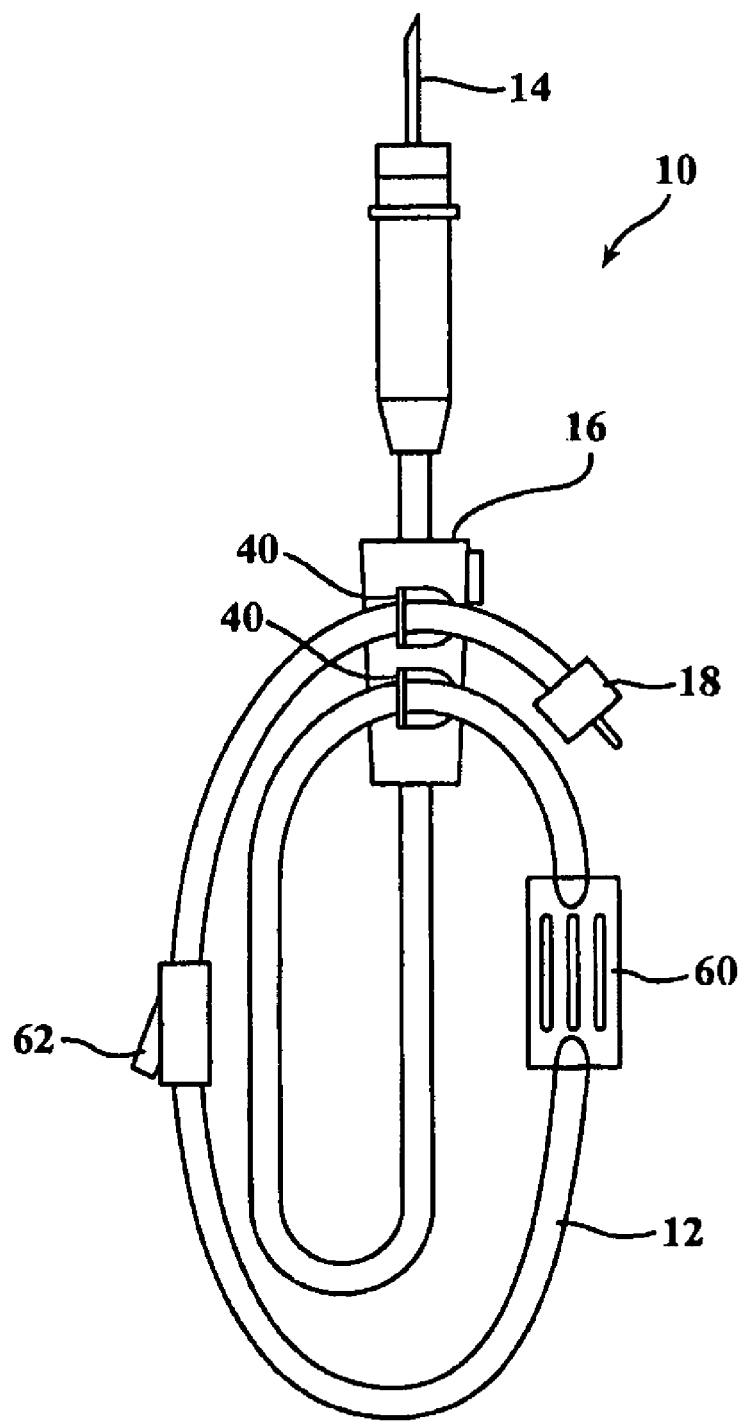
FIG. 8 is a perspective view of an implementation of an IV component modified to include a plurality of clips to retain the IV administration set in a desire configuration.

Referring now to FIG. 7, multi-sectional organizer 430 is shown. The multi-sectional organizer 430 comprises a first organizing section 432 and a second organizing section 434, each section 432 and 434 being separate and distinct from the other. The first organizing section 432 includes a first organizing surface 22 upon which a portion of the IV set 10 is retained in a desired configuration. Similarly, the second organizing section 434 includes a second organizing surface 24 upon which a portion the IV set 10 is retained in a desired configuration. Benefits associated with the multi-sectional organizer 430 include decreased product materials, as well as the ability to maneuver, collapse, and compress the retained IV set 10 and organizer 430 to aid in packaging, portability, storage, and shipment. Following the priming procedure of the IV set 10, the terminal end 18 is pulled in a downward direction to manually pull the intravenous tubing 12 from the clips 40. In some embodiments, the IV set 10 remains in the organizer 430 following the priming procedure, and throughout the remaining use of the IV set 10 for infusion procedures.

Referring now to FIG. 8, an IV component 16 of the IV administration set 10 is modified to include a plurality of clips 40 for retaining the IV set 10 in a desired configuration. In some embodiments the clips are attached directly to an outer surface of the component 16 via an adhesive or a mechanical connection. In other embodiments, a portion of the outer surface of the component 16 is molded, or otherwise manufactured to provide the clips 40. In this way, the component 16 performs multiple functions, including organizing the IV set 10 into a desired configuration, monitoring flow though the intravenous tubing 12, and ensuring proper orientation of the IV components of the IV set 10. Other embodiments include additional clips on other components of the IV set 10 to provide additional options and configuration. As such, the additional clips enable the a user to achieve desired orientations of the intravenous tubing 12 and the various IV components as required for efficient priming of the system.

Figure 9:
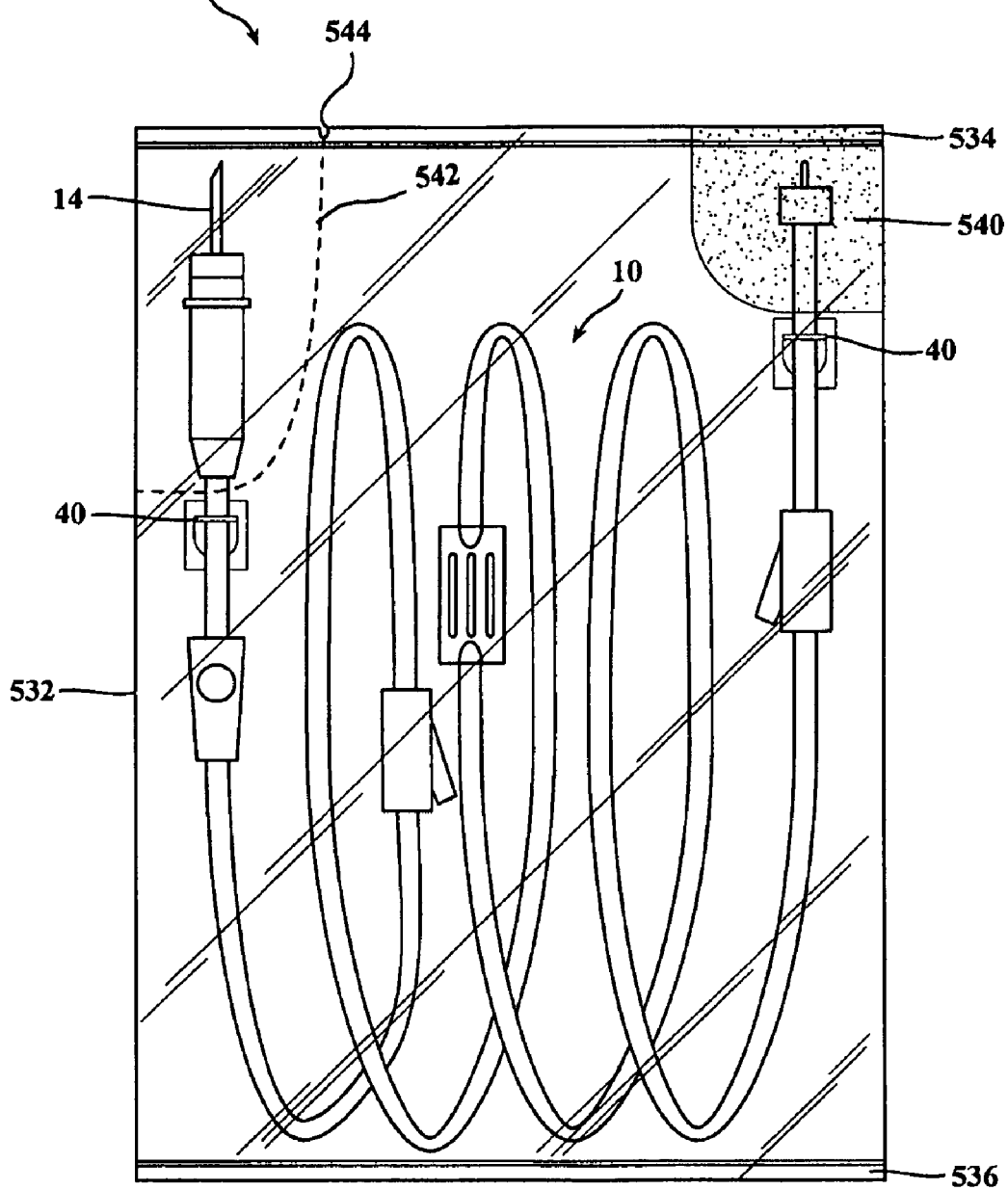
FIG. 9 is a perspective view of an implementation of a package organizer containing and retaining an IV administration set in a desired configuration.

Referring now to FIG. 9, a package organizer 530 is shown. The package organizer 530 includes an outer packaging material 532 such as a polymer bag, a paper bag, or a polymer lined paper bag. In some embodiments, the packaging material 532 is sealed both at an upper edge 534, at a lower edge 536. In some embodiments the upper and lower edges 534 and 536 are sealed via plastic welding or an adhesive. In other embodiments the upper and lower edges 534 and 536 are sealed via an interlocking zipper or closure. In some embodiments, the package organizer 530 includes a molded, plastic shell (not shown) and a removable backing material, such as a sheet of paper, a polymer sheet, or a polymer lined sheet of paper (not shown). In these embodiments, the backing material is attached to the plastic shell via a perimeter edge of the backing material, and the IV set 10 is positioned within a space between the backing material and the plastic shell.

In some embodiments of the present invention, the interior of the sealed package organizer 530 is sterile or waterproof to protect the contents of the package. The package organizer 530 is generally sized and configured to adequately house an IV administration set 10. The package organizer 530 further include at least two clips 40 to secure a first end 14 and a terminal end 18 of the IV set in a desired position within the packaging material 532. The two clips 40 are attached to the packaging material 532 so as to position the first end 14 and the terminal end 18 of the IV set in desirable locations within the package organizer 530. For example, in some embodiments it is desirable to control the position of the first end 14 of the IV set 10 in an upper left corner of the package organizer 530. As such, the clip 40 is attached to the packaging material 532 in a position proximal to the upper left corner. The first end 14 is then secured to the packaging material 532 via the clip so as to position the first end 14 in the upper left corner of the package organizer 530. In other embodiments, controlled positioning of the terminal end 18 in the upper right corner of the package organizer 530 is accomplished via a similar process.

Having controlled the first end 14 and the terminal end 18 via the clips 40, the intravenous tubing 12 and the remaining components of the IV set are maintained within the package organizer 530 in a desired configuration. In some embodiments, additional clips (not shown) are provided at other positions along the IV set 10 to secure the IV set 10 within the package organizer 530 is a desired configuration. As such, the configuration of the IV set 10 within the package organizer 530 achieves desired orientations for the various components of the IV set 10.

In some embodiments, the packaging material 532 further includes markings 540 and features 542 to aid a user in locating and accessing desired portions of the IV administration set 10. For example, in some embodiments a portion of the packaging material 532 proximal to fixed position of the terminal end 18 is marked with a configuration or color 540. This marking 540 provides a visual indicator as to the position of the terminal end 18 within the package organizer 530. The marking 540 permits the user to quickly locate the controlled location of the terminal end 18, and correctly orient the package organizer 530 as desired.

In other embodiments, the packaging material 532 further includes a feature 542 to aid the user in accessing the first end 14 of the IV set 10. For example, in some embodiments a portion of the packaging material 532 proximal to the fixed position of the first end 14 is perforated 542. The perforation 542 permits the user to easily tear open the package organizer 530 to access the first end 14. The perforation 542 further provides a visual and tactile indicator of the fixed position of the first end 14 within the package organizer 530. In some embodiments, a nick or partial tear 544 of packaging material 532 is provided near the fixed position of the first end 14. As such, a user may use the nick 544 as a starting point for tearing open the package organizer 530 to access the first end 14 of the IV set 10. In some embodiments where it is desirable to maintain the IV set 10 in a sealed, sterile environment, a nick 544 is preferred over the perforation 542 feature. Finally, in some embodiments a combination of markings 540 and features 542 and 544 are used to provide visual and tactile indicators for a user of the package organizer 530.

The features of the present invention provide improved methods for preparing and priming an IV administration set for use with a patient. In some embodiments of the present invention an improved method for preparing the IV set includes the steps of opening highlighted or marked portions of the packaging material to locate a clamp of the IV set; engaging the clamp to occlude flow through the IV set; opening a highlighted or marked portion of the packaging material to locate the spike component of the IV set; attaching the spike component to a fluid reservoir and allowing the device retaining the IV set to hang from the fluid reservoir; opening a highlighted or marked portion of the packaging material to locate the terminal end of the IV set; attaching the terminal end to any extension set, stopcock, or other addition to the IV set; priming the drip chamber; opening the clamp to initiate flow through the IV set to prime the IV set; pulling the terminal end from the device wherein the IV set unzips from the device as the clips release; removing the terminal end dust cap and connecting the terminal end to the patient. In some embodiments, the terminal end dust cap further includes an auto-prime filter that is permeable to air but prevents the passage of liquid. As such, the auto-prime filter permits the IV system to optimally prime by exhausting air within the IV set, yet prevents liquid from exiting the terminal end.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A device for organizing an IV administration set, the device comprising:
    a planar organizing surface on which an IV administration set is supported in a desired configuration
    wherein a first portion of the unprimed IV administration set is supported in a priming configuration direction, wherein a first portion of the unprimed IV administration set is oriented for a downward flow, and a second portion of the unprimed IV administration set is oriented for an upward flow, a transition portion of the unprimed IV administration set being positioned between the first and second portions; and
    a plurality of retaining mechanism each having a planar portion comprising a cut-out portion of the organizing surface, the retaining mechanisms planar portion having a first position within a plane of the organizing surface and a second position outside of the plane of the organizing surface, the retaining mechanisms being positioned and oriented on the organizing surface to support the IV administration set in the desired configuration.

2. The device of claim 1, further comprising an IV component integratedly coupled to a tubing portion of the IV administration set.

3. The device of claim 1, wherein the organizing surface and the retaining mechanisms comprise a unitary board structure.

4. The device of claim 1, further comprising a packaging in which the device is contained, and wherein the organizing surface forms a portion of the packaging.

5. The device of claim 1, wherein the plurality of retaining mechanisms is selected from the group consisting of a clip, a clamp, an adhesive, a catch, and a hook.

6. The device of claim 1, wherein the plurality of retaining mechanisms further comprises a first retaining mechanism in a first orientation, and a second retaining mechanism in a second orientation, wherein the first orientation is transverse to the second orientation.

7. The device of claim 2, wherein an outer surface of the IV component comprises the organizing surface and the retaining mechanism.

8. The device of claim 2, wherein the IV component further comprises a desired priming orientation, and the desired configuration maintains the desired priming orientation.

9. The device of claim 3, comprising a plurality of board structures.

10. A device for storing an IV administration, the device comprising:
    an organizing surface on which an unprimed IV administration set is supported in a priming configuration, wherein a first portion of the unprimed IV administration set is oriented for a downward flow, and a second portion of the unprimed IV administration set is oriented for an upward flow, a transition portion of the unprimed IV administration set being positioned between the first and second portions; and
    a plurality of retaining mechanisms each comprising a cut-out portion of the organizing surface, a first retaining mechanism of the plurality of retaining mechanisms having a first orientation for supporting the first portion of the unprimed IV administration set for the downward flow, a second retaining mechanism of the plurality of retaining mechanisms having a second orientation for supporting the second portion of the unprimed IV administration set for the upward flow, and a third retaining mechanism of the plurality of retaining mechanisms having a third orientation for supporting the transition portion of the unprimed IV administration set, wherein the third orientation is transverse to the first and second orientations;

and a plurality of retaining mechanism each having a planar portion comprising a cut-out portion of the organizing surface, the retaining mechanism planar portion having a first position within a plane of the organizing surface and a second position outside of the plane of the organizing surface, the retaining mechanisms being positioned and oriented on the organizing surface to support the IV administration set in a desired configuration.

* * * * *